(12) United States Patent
Muehlsteff et al.

(10) Patent No.: US 7,424,319 B2
(45) Date of Patent: Sep. 9, 2008

(54) ELECTRODE ASSEMBLY AND A SYSTEM WITH IMPEDANCE CONTROL

(75) Inventors: Jens Muehlsteff, Aachen (DE); Harald Reiter, Aachen (DE); Andras Montvay, Stuttgart (DE); Josef Lauter, Geilenkirchen (DE); Olaf Such, Aachen (DE); Ralf Schmidt, Aachen (DE); Michael Perkuhn, Aachen (DE); Fabian Kohler, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 186 days.

(21) Appl. No.: 10/539,353

(22) PCT Filed: Nov. 24, 2003

(86) PCT No.: PCT/IB03/05481

§ 371 (c)(1),
(2), (4) Date: Jun. 15, 2005

(87) PCT Pub. No.: WO2005/089727

PCT Pub. Date: Sep. 29, 2005

(65) Prior Publication Data

US 2006/0111624 A1    May 25, 2006

(30) Foreign Application Priority Data

Dec. 19, 2002  (EP) .................... 02080431

(51) Int. Cl.
*A61B 5/04* (2006.01)
*A61N 1/05* (2006.01)
(52) U.S. Cl. .............. 600/372; 600/397; 607/153
(58) Field of Classification Search ............ 600/372
See application file for complete search history.

(56) References Cited

U.S. PATENT DOCUMENTS

| | | | | |
|---|---|---|---|---|
| 3,340,868 A | * | 9/1967 | Darling ............... | 600/392 |
| 4,166,457 A | * | 9/1979 | Jacobsen et al. ....... | 600/397 |
| 4,274,419 A | * | 6/1981 | Tam et al. ............ | 600/372 |
| 4,311,152 A | * | 1/1982 | Modes et al. ......... | 600/392 |
| 5,628,729 A | * | 5/1997 | Okabe ................ | 604/20 |
| 6,374,138 B1 | | 4/2002 | Owen et al. | |
| 6,640,118 B2 | * | 10/2003 | Van Heerden et al. .... | 600/372 |

* cited by examiner

*Primary Examiner*—Lee S Cohen

(57) ABSTRACT

An electrode assembly arranged to carry out a bioelectrical interaction with an individual, said electrode assembly comprising a conductive material having a contact surface arranged to be brought into contact with a receiving area of the individual's skin, said conductive material being electrically connectable to a suitable electronic device to enable said interaction, the electrode assembly having an impedance control means arranged to measure and control the impedance of the receiving area of the individual's skin prior to an event of the bioelectrical interaction.

9 Claims, 2 Drawing Sheets

ELECTRODE ASSEMBLY AND A SYSTEM WITH IMPEDANCE CONTROL

Figure 1:
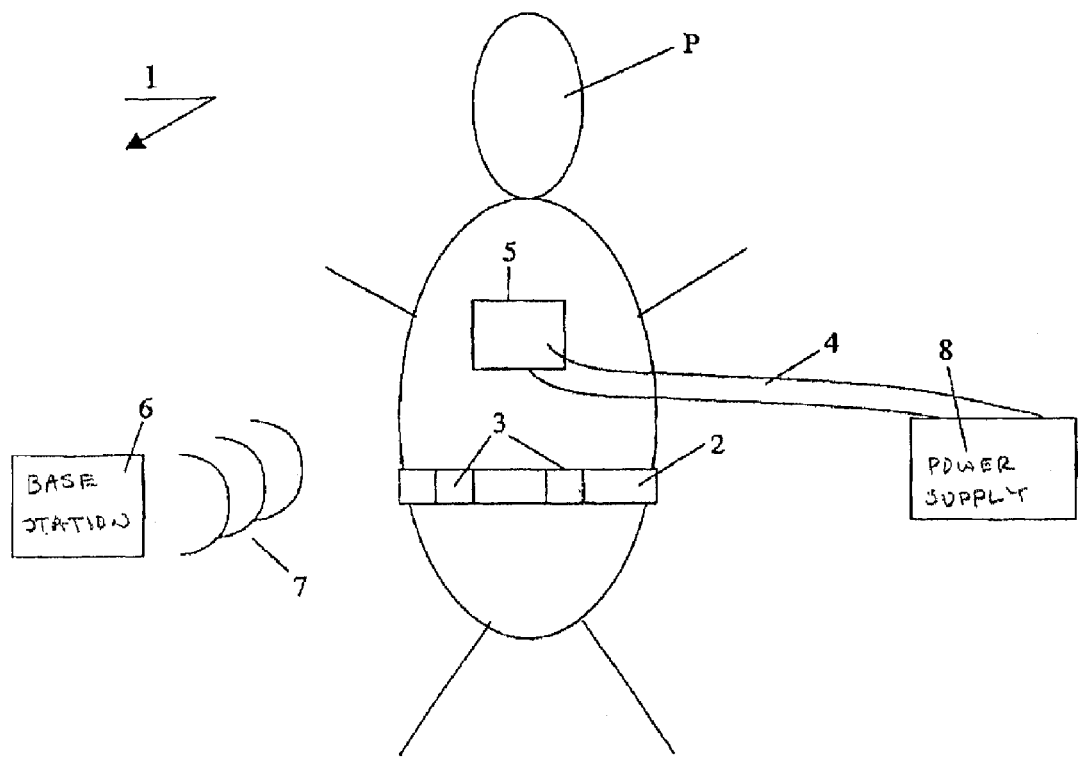

The invention relates to an electrode assembly arranged to carry out a bioelectrical interaction with an individual, said electrode arrangement comprising a conductive material having a contact surface arranged to be brought into contact with a receiving area of the individual's skin, said conductive material being electrically connectable to a suitable electronic device to enable said interaction.

The invention further relates to a system for enabling a bioelectrical interaction with an individual.

An electrode assembly as set forth in the opening paragraph is known from U.S. Pat. No. 6,374,138. The known electrode assembly is arranged to enable the bioelectrical interaction with the individual by means of a monitoring of an electrical signal characteristic to an activity of a user, for example an electrocardiogram. The known electrode assembly is further suitable to carry out a myostimulation or an application of a defibrillation discharge. The known electrodes are of a so-called dry type, where no specific electrolyte is applied in a space between the contact surface of the electrode and the individual's skin. In this way a naturally produced body fluid, like sweat is used as the electrolyte to ensure a suitable electrical conductivity in an interface between the electrode and the individual's skin.

A disadvantage of the known electrode assembly is that the sweat production of the individual cannot be controlled resulting in a necessity for measures to ensure a further increase of the conductivity. In the known electrode arrangement therapeutic and/or prophylactic agents for purposes of skin conditioning can be used in the space between the contact surface of the electrode and the skin. The substances put forward as suitable agents in U.S. Pat. No. 6,374,138 are electrically conductive in their nature, however the application thereof does not achieve an improvement of the electrical properties at the interface between the electrode and the skin in a predetermined and efficient way.

It is an object of the invention to provide an electrode assembly suitable for carrying out a bioelectrical interaction with the individual, the assembly providing an improved controllability of the electrical properties of the electrode-skin interface.

The electrode assembly according to the invention is characterized in that said electrode assembly comprises impedance control means arranged to control the impedance of the receiving area of the individual's skin prior to an event of the bioelectrical interaction. Naturally, in order to carry out the impedance control, it is desirable that the initial value of the impedance be determined. This can be achieved by a per se known measuring circuit, which will be discussed with reference to FIG. 4. The dry-electrodes utilize the naturally produced sweat as an electrolyte to ensure a suitable electrical contact between the electrode and the skin. For some applications the sweat production is too slow causing an increase of current densities to be applied for suitable bioelectrical interaction, for example for purposes of defibrillation. In a monitoring application insufficient conductivity of the electrode-skin interface results in a poor signal to noise ratio, which may cause a decrease in the performance of the electrode assembly as a whole. According to the technical measure of the invention the electrical parameters can be controlled in an active way. This is of particular importance for purposes of durable application of the electrode assembly. Next to this, as skin resistance, sweat production, chemical composition of the sweat are strongly dependent on the individual, these parameters can be equalized using the impedance control means according to the invention, yielding improved systems for bioelectrical interaction adapted for use by different individuals. Additionally a reduction of a production cost of such a system is achieved as the number of different electrode types is reduced. The standard electrode types can be adjusted by a proper electrolyte choice.

An embodiment of the electrode assembly according to the invention is characterized in that the impedance control means comprises a depot of a conductive fluidum and an actuatable discharge means arranged to discharge said fluidum in a space between the contact surface and the receiving area. According to this technical measure the electrolyte is applied to the interface electrode-skin on demand. The electrode properties are adjustable by a suitable choice of the conductive fluidum. For an automatic increase of conductivity it is preferable to use a pumping system comprising an electrically driven pump together with a depot of an electrolyte. Advantage of this solution is that it can be refilled and reused as well as enables a continuous automatic control of skin-electrode impedance.

A further embodiment of the electrode assembly according to the invention is characterized in that the contact surface of the conductive material comprises a conductive rubber layer provided with pores, the impedance control means comprising a container with an ignitable pressurized gas arranged to induce a force on said depot in a direction of the pores upon an event of an ignition. The depot can be arranged inside or outside the body of the conductive material. Preferably, the conductive material comprises a conductive rubber, however other suitable conductive materials or structures like mesh can be used as well. In case of shortly required increased conductance, e.g. defibrillation by a shock, the impedance control means initiates ignitions of a priming charge and the expanding gases press the electrolyte through pores between skin and electrode. After this event the priming charge and the electrolyte can be replaced. It must be understood that under the term 'pores' any fluidim-conducting structures are meant. Examples of suitable pores are ducts, channels, micro-holes and cavities.

A still further embodiment of the electrode assembly according to the invention is characterized in that the contact surface of the conductive material is formed by a compartment housing said depot, the discharge means comprising a settable fiber located in said compartment and extending in a direction transversal to the contact surface. Preferably textiles are used in which electrolyte depots can be placed. The depots can be arranged to comprise capsules which can be erupted in different ways. There are fibers implemented into the textiles, which can be shorted by applying an electrical voltage. The capsules erupt and the conductive fluidum will be emitted. Using capsules with different sensitivities of exerting forces the flow can be adjusted according different requirements. Alternatively, a heating system is implemented into the textile and if needed the fibers can be heated up and the capsules will be erupted.

These and other aspect of the invention will be explained with reference to figures.

FIG. 1 present in a schematic view an embodiment of a system for enabling a bioelectrical interaction with the individual.

Figure 2:
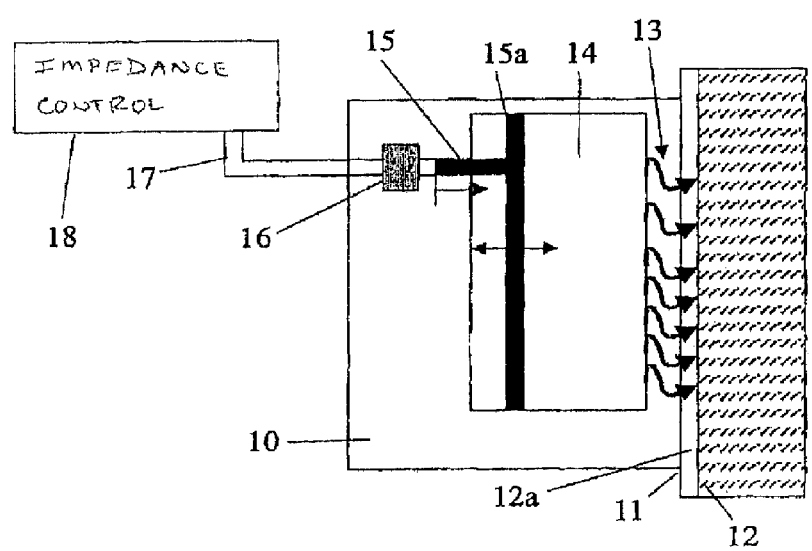

FIG. 2 presents in a schematic view an embodiment of an electrode assembly with the impedance control means according to the invention.

Figure 3:
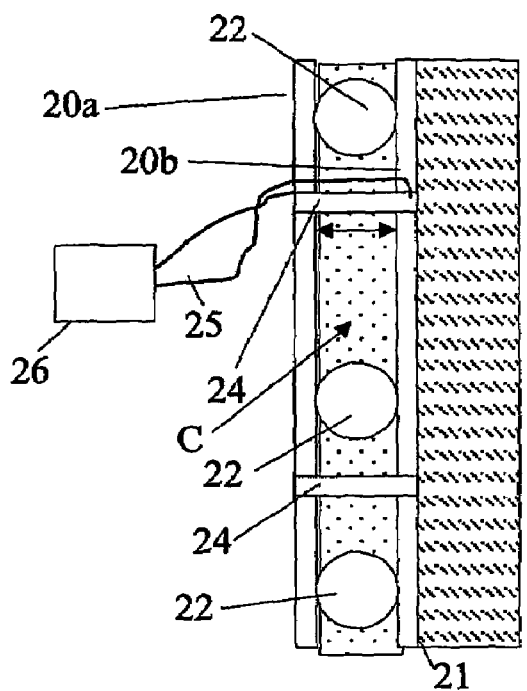

FIG. 3 presents in a schematic view a further embodiment of an electrode assembly with the impedance control means according to the invention.

Figure 4:
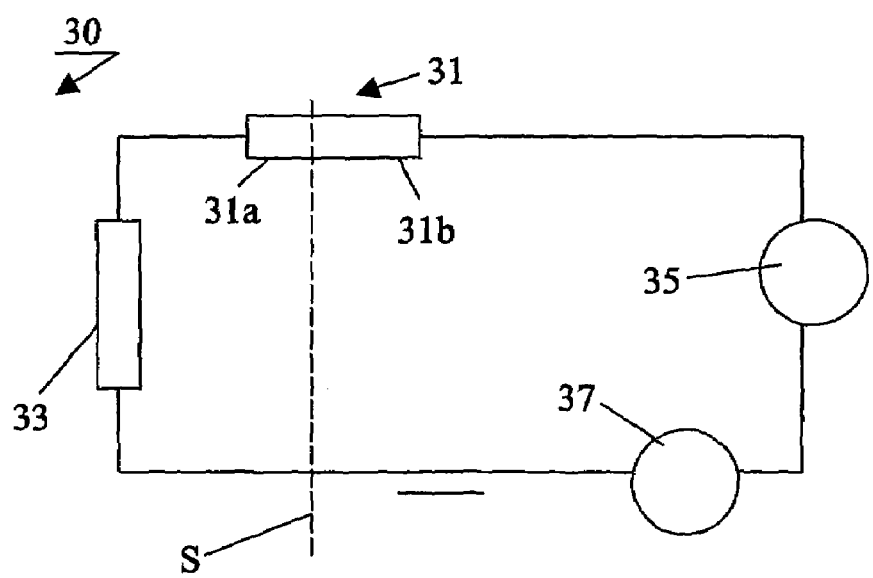

FIG. 4 presents a schematic view of an embodiment of an impedance sensing means.

FIG. 1 present in a schematic view an embodiment of a system for enabling a bioelectrical interaction with the individual.

FIG. 1 presents a schematic view of an embodiment of the wearable monitoring system 1. A patient P is supplied with a set of sensors 3, integrated on a carrier, for example an elastic belt 2. The set of sensors 3 are reliably positioned in contact with the patient's skin in order to acquire a desirable physiological signal. For example, such a monitoring system can be arranged to perform measurements of the heart activity or a signal derived from the heart activity. The sensors 3 comprising electrodes (not shown) are typically electrically connected to a storage and analysis device SAD (not shown). The SAD is arranged to perform a primary data analysis in order to interpret the acquired physiological data. The data analysis is being performed by means of a conditioning and interpreting circuitry (not shown). In case the conditioning and interpreting circuitry detects a life threatening abnormality (for example an arrhythmia condition or a cardiac arrest) a control signal, for example, an alarm is being sent to a base station 6. The base station 6 is arranged to interact with a medical emergency center (not shown). The base station 6 can be further arranged to actuate a further bioelectrical interaction with the user by means of a wireless signal 7. For example, the wireless signal 7 can be arranged to actuate a defibrillating event by means of the electrode set 5 electrically connected to a power supply unit 8 by means of suitable power lines 4. Prior to the event of defibrillation it may e necessary to adapt the interface between the contact surface of the electrodes 5 and the patient's skin. This can be achieved by means of the impedance control means according to the invention, which is explained in further detail with reference to FIG. 2.

FIG. 2 presents in a schematic view an embodiment of an electrode assembly with the impedance control means according to the invention. The electrode 10 comprising the contact surface 11 is brought into contact with the individual's skin 12. In general the contact surface 11 will not perfectly close on the skin, leaving a inter space 12a. When the electrode 10 is applied to the surface 12 for a durable amount of time, the inter space 12a will be substantially filled with sweat produced by the individual due to transpiration. In case the sweat does not fill the inter space 12a completely it is filled with air, leading to a poor electrical contact between the electrode 10 and the skin 12. In order to improve the impedance of the inter space 12a, the electrode assembly according to the invention comprises an electrolyte depot 14 filled with a dischargeable electrolyte. The discharge of the electrolyte is performed on demand by means of the impedance control means 18 arranged to send a trigger signal over the electrical connection wires 17 to the discharge means 16. In this example the discharge means 16 are arranged to initiate an expansion of a pressurized gas 15 stored in a body of the electrode 10. The effect of a gas expansion is similar to the effect of an air bag as used in the car, however on a different scale. The expanded gas travels through a gas transport channel 15a and causes the electrolyte 14 to flow out of the body of the electrode 10 via pores 13 into the inter space 12a. The operation of the impedance control means 18 can be controlled by a sensor (not shown) which is arranged to measure the actual impedance of the inter space 12a. In case the actual value of the impedance of the inter space 12a is lower then a preset threshold the impedance control means 18 are actuated by the system electronics (not shown) to trigger the electrolyte discharge.

FIG. 3 presents in a schematic view a further embodiment of an electrode assembly with the impedance control means according to the invention. The body of the electrode (not shown) conceived to be positioned in contact with the patient's skin 21 is formed by a compartment C housing the electrolyte depot. Preferably, the electrolyte depot comprises a plurality of capsules 22 with an enclosed electrolyte. The compartment C is delineated by a textile layers 20a and 20b. The advantage of using textile is that the textile as such has micropores due to a thread pattern which can be used to transport the electrolyte form erupted capsules to the surface of the skin 21. In order to erupt the electrolyte capsules 22 the compartment C comprises fibers 24 which are made of a settable material. The impedance control means 26 are arranged to provide an actuation signal to the fibers 24 in order to shrink them. It is possible to use materials which decrease their dimension under an application of a voltage or a temperature (electrostriction). This can be achieved by means of wiring 25 which conducts a suitable actuation trigger to the fiber material. When the fibers shrink, the capsules erupt under the influence of the generated pressure of the fabric layer 20a and the electrolyte flows through the layer 20b towards the skin 21. Typically, the capsules with dimensions of the range of nano- to micrometer diameter are suitable. It is possible to use capsules with different surface rigidity to enable a stepwise electrolyte discharge. A different approach is to heat up the area near the compartment housing the capsules. In this embodiment the setting fibers can be omitted. This can be achieved by conducting heat to the textile layers 20a, 20b. The capsules will burst due to thermal expansion and the electrolyte will flow through the layer 20b to the contact surface 21.

FIG. 4 presents a schematic view of an embodiment of an impedance sensing means. A typical equivalent circuit 30 of an electrode 31 placed on a body surface S can be presented as a series connection of the body impedance 33 and the electrode impedance 31. Impedance of electrode 31 is divided into a skin—part 31a and a pure electrode part 31b. The impedance of tissue 33 is in general much lower than that of the electrode 31. There is also a capacitive part of the impedance for tissue and the electrodes (not shown). The sensing principle is to apply a AC-voltage on the electrodes by means of a power supply source 35. Alternatively, an AC-current can be induced by a current source (not shown). The present embodiment shows an operation of the impedance sensing means in case a power supply source is used. The equivalent circuit 30 comprises further an amperemeter 37 arranged to measure the current or drop in the circuit 30. The impedance can be estimated from this measurement. A method to estimate the impedance is known for a person skilled in the art and will not be explained in further details. In case a measured value of the impedance is higher than a predetermined threshold value, the a trigger signal (not shown) is sent to the impedance control means (not shown) in order to discharge an additional electrolyte to the skin surface S.

The invention claimed is:

1. An electrode assembly arranged to carry out a bioelectrical interaction with an individual, said electrode assembly comprising a conductive material having a contact surface arranged to be brought into contact with a receiving area of the individual's skin, said conductive material being electrically connectable to a suitable electronic device to enable said interaction, characterized in that said electrode assembly comprises impedance control means arranged to measure and control the impedance of the receiving area of the individual's skin prior to an event of the bioelectrical interaction, the impedance control means including a depot of a conductive fluidum and an actuatable discharge means arranged to discharge said fluidum in a space between the contact surface and the receiving area.

2. An electrode assembly according to claim 1, characterized in that the contact surface of the conductive material comprises a layer provided with pores, the impedance control means comprising a container with an ignitable pressurized gas arranged to induce a force on said depot in a direction of the pores upon an event of ignition.

3. An electrode assembly according to claim 1, characterized in that the contact surface of the conductive material is formed by a compartment housing said depot, the discharge means comprising a settable fiber located in said compartment and extending in a direction transversal to the contact surface.

4. An electrode assembly according to claim 3, characterized in that the settable fiber comprises an electrostrictive material.

5. An electrode assembly according claim 3, characterized in that the settable fiber comprises a thermoelectric material.

6. An electrode assembly according to claim 1, characterized in that the conductive material comprises a conductive fabric.

7. A system for enabling a bioelectrical interaction with an individual, said system comprising an electrode assembly according to claim 1 and a power supply unit electrically connected to the electrode assembly.

8. A system according to claim 7, further comprising a vital sign monitoring means for measuring an electrical signal on the body of an individual.

9. A system according to claim 7, further comprising a means for inducting electrical current in the body of the individual.

* * * * *